United States Patent
Mizutani et al.

(10) Patent No.: US 7,160,278 B2
(45) Date of Patent: Jan. 9, 2007

(54) AUXILIARY PAD FOR MOUNTING ABSORBABLE ARTICLE

(75) Inventors: Satoshi Mizutani, Kagawa (JP); Koichi Yamaki, Kagawa (JP); Yuki Noda, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 28 days.

(21) Appl. No.: 10/888,541

(22) Filed: Jul. 8, 2004

(65) Prior Publication Data

US 2005/0004546 A1 Jan. 6, 2005

Related U.S. Application Data

(63) Continuation of application No. PCT/JP02/12014, filed on Nov. 18, 2002.

(51) Int. Cl.
*A61F 13/15* (2006.01)

(52) U.S. Cl. ............ 604/385.14; 604/386; 604/385.01; 604/385.11

(58) Field of Classification Search ........... 604/385.01, 604/378, 385.11, 385.14, 386, 393, 395
See application file for complete search history.

(56) References Cited

U.S. PATENT DOCUMENTS

| | | | |
|---|---|---|---|
| 5,507,735 A * | 4/1996 | Van Iten et al. | 604/385.05 |
| 6,114,597 A * | 9/2000 | Romare | 604/378 |
| 6,508,795 B1 * | 1/2003 | Samuelsson et al. | 604/378 |
| 2001/0021834 A1 | 9/2001 | Yoshimasa | |
| 2002/0120247 A1 | 8/2002 | Mizutani et al. | |

FOREIGN PATENT DOCUMENTS

| | | |
|---|---|---|
| EP | 0 985 397 A2 | 3/2000 |
| JP | 1-119631 | 8/1989 |
| JP | 06-254116 | 9/1994 |
| JP | 10-127692 | 5/1998 |
| JP | 2000-325395 | 11/2000 |
| JP | 2001-245921 | 9/2001 |
| JP | 2001-245925 | 9/2001 |
| JP | 2002-165833 | 6/2002 |
| JP | 2002-315776 | 10/2002 |
| JP | 2003-038560 | 2/2003 |
| WO | WO-00/13640 A1 | 3/2000 |

\* cited by examiner

*Primary Examiner*—Jacqueline F. Stephens
(74) *Attorney, Agent, or Firm*—Darby & Darby (57) ABSTRACT

The present invention concerns an auxiliary pad for absorbent article that can prevent body fluid from leaking along with the dislocation of an absorbent article such as sanitary napkin, and provides a hygienic article that can reduce the occurrence of body fluid leak, even when the dislocation of fitting happens, all the way securing a sufficient adhesion to the inside of the thigh.

An auxiliary pad for absorbent article (2), comprising an absorbent sheet body (5) adhered to the inside of the thigh of the wearer for absorbing body fluid, a linkage stem body (9) for linking the absorbent sheet body and an junction sheet body (7), and the junction sheet body (7) to which an adhesive (6) is applied, is attached to a sanitary napkin (10) to constitute a sanitary article (1).

11 Claims, 11 Drawing Sheets

AUXILIARY PAD FOR MOUNTING ABSORBABLE ARTICLE

CROSS-REFERENCE TO RELATED APPLICATIONS

This application is a Continuation of International Application No. PCT/JP2002/012014 filed Nov. 18, 2002, which application published in Japanese on Jun. 3, 2004 as WO 2004/045475 A1 under PCT Article 21 (2).

FIELD OF THE INVENTION

The present invention relates to a hygienic article for the absorbent article for preventing body fluid from leaking by dislocation of any absorbent article such as sanitary napkin or others.

BACKGROUND ART

Conventionally, the absorbent articles including an absorbent body such as a sanitary napkin are used widely as sanitary article for body fluid absorption. Here, especially for highly demanded sanitary napkins, a great deal of effort went into the prevention of menstrual blood from leaking. In addition, various contrivances have been applied in order to prevent the wearing point from moving.

However, as the sanitary napkin is basically attached to an underwear, and is not designed to be worn in a close contact with the inside of the thigh of a wearer, a gap is created easily between the ostium vaginae and the napkin, allowing the menstrual blood to leak. In this point, as an auxiliary of a sanitary napkin for absorbing menstrual blood, Japan Utility Model Publication No. HEI 1-119631 discloses a small sanitary napkin to be used over a sanitary napkin, while Laid-Open Japanese Patent Publication No. HEI 10-127692 discloses a stick-like auxiliary absorbent to be used with a sanitary napkin by sandwiching between the haunches. As all of these auxiliaries are destined to fill the gap generated between the inside of the thigh of the wearer and the napkin, it can be said that they provide a higher menstrual blood leak prevention function, compared to the case where the napkin is used solely.

Nevertheless, these auxiliaries may deform due to compression according to the body motion of the wearer such as walking or to being wet by a prolonged wearing, and it is feared that the face of an auxiliary in contact with the body is no more closely applied to the crotch of the wearer. In such a case, a gap is generated between the auxiliary and the body, menstrual blood leaks easily from the gap, and its function to assist the sanitary napkin to prevent leakage will not be deployed sufficiently.

As improvement against such deformation of the auxiliary after wearing, Laid-Open Japanese Patent Publication No. 2000-325395 discloses a stick-like pad made of an elastic layer with a hollow interior. However, as this auxiliary only has a structure where an elastic member is simply arranged hollow, it is feared that the elastic layer collapses and if it becomes the case, the absorption capacity lowers, and menstrual blood leakage can not be prevented sufficiently.

Moreover, as all of the aforementioned auxiliaries are supposed to be used affixed to a sanitary napkin, in case where a dislocation or a deformation such as torsion is generated in the sanitary napkin by the activity of the wearer, they will also turn up to be dislocated or deformed together.

Furthermore, as the aforementioned is affixed to the sanitary napkin, even when the sanitary napkin is not soiled, it becomes necessary to change not only the auxiliary but also the sanitary napkin and the unnecessary change unintentionally increases the burden of the wearer.

Due to these factors, actually, the conventional auxiliary for the absorbent article mentioned above does not come to reduce the occurrence of body fluid leak by the dislocation of fitting and secure a sufficient adhesion to the inside of the thigh.

The present invention has been made in view of inconveniences as mentioned above and has an object of providing a hygienic article that could reduce the occurrence of body fluid leak, even when the dislocation of fitting happens, all the way securing a sufficient adhesion to the inside of the thigh.

Another object of the present invention is to provide a sanitary article that can plan to prevent appropriately the menstrual blood from leaking, independently of collapse or deformation provoked by the pressure from femoral region of the wearer.

DISCLOSURE OF THE INVENTION

In order to solve the aforementioned inconveniencies, the present invention is characterized by that the absorption efficiency of the absorbent body is improved by reducing the size of the auxiliary and allowing it to move flexibly and at the same time, the possibility of occurrence of body fluid leakage is lowered remarkably by allowing the auxiliary to move freely following the motion of the wearer, and more particularly, the absorbent sheet body positioned in contact with the crotch is attached to an absorbent article through a linkage stem body.

It is also characterized by that only the auxiliary can be exchanged leaving the absorbent article as it is, by making the linkage stem body detachable.

To be more specific, the present invention provides that which is described below.

(1) 1. An auxiliary pad for attaching to an absorbent article, comprising:

an absorbent sheet body including an absorbent body for absorbing liquid and a cover sheet for covering the absorbent body, a junction sheet body having an adhesive layer for attaching to the absorbent article, and a linkage stem body for linking said absorbent sheet body and the junction sheet body, In such auxiliary pad for attaching to the absorbent article according to the present invention, the absorbent sheet body for absorbing body fluid such as menstrual blood and the junction sheet body for holding the absorbent sheet body in the absorbent article are connected by the linkage stem body having such a flexibility that can prevent them from moving together, and the absorbent sheet body is not affixed directly to the absorbent article. Consequently, even if the absorbent article attached to an underwear moves along with the action of the wearer such as waling, the absorbent article would not move together with that.

In short, as the linkage stem body is flexible, it will not follow the displacement of the absorbent article and can remain in the crotch. Furthermore, even if the absorbent article slips off relatively in respect to the inside of the thigh of the wearer, only the linkage stem body deforms flexibly, and the absorbent sheet body would not slip off. As a result, the absorbent sheet body can be maintained in a state positioned in contact with the inside of the thigh of the wearer, allowing to reduce the occurrence of body fluid leak by the dislocation of fitting of the absorbent article.

Also, according to the present invention, due to the presence of the linkage stem body, the absorbent sheet body is out of a state of close adhesion on the body side face of the absorbent article.

In this point, as for the prior art where practically two absorbent bodies are only overlaid in a close contact, body fluid would not be absorbed by the absorbent article in a portion where an auxiliary is affixed, in case of saturation of the surface of the auxiliary faced to the body side, making a combination of two layers meaningless from the viewpoint of improvement in body fluid absorption efficiency.

On the contrary, as for the present invention, from a macroscopic point of view, two absorbent bodies are overlaid; however, from a microscopic point of view, the auxiliary pad is not adhered to the absorbent article, enlarging the range of body fluid absorption capability of the absorbent article, compared to a case where an auxiliary is attached directly to the absorbent article as in the prior art. As a result, both auxiliary pad and the absorbent article can absorb body fluid efficiently.

As the auxiliary pad according to the present invention is not formed integrally with the absorbent article, it can be made detachable, by adopting a material that can be pealed off all the way limiting fluff on the surface of the absorbent article as adhesive used for the adhesive layer of the junction sheet body. If it is the case, when the quantity of spilling body fluid is limited, only the auxiliary pad according to the present invention can be exchanged, leaving the absorbent article as it is. Therefore, it is enough for the wearer to carry only a spare auxiliary pad on her, which is convenient for portability.

The longitudinal length dimension of the "linkage stem body" might be the one that have a length dimension equivalent to the longitudinal direction of the absorbent sheet body; however, it may be a dimension shorter than the absorbent sheet body, provided it is equal or superior to two thirds of the full length at least in respect of the absorbent sheet body. It should be appreciated that, if the linkage stem body is provided to have this dimension, it can be disposed partially, other than in a serial disposition. Besides, the dimension of the "linkage stem body" in the lateral direction is preferably in a range of 0.5 mm to 30 mm, depending on the thickness of the material. With the adoption of such length dimensions, an appropriate deformation can be realized according to the motion of the wearer.

As for the appearance shape of the "absorbent sheet body", one that can fit suitably to the crotch of the wearer can be selected conveniently from rectangular shape, oval shape, sandglass shape and so on.

The full length dimension in the longitudinal direction of the absorbent sheet body is set preferably in a range of 60 to 200 mm and, more preferably in a range of 80 to 150 mm. On the other hand, the dimension in the lateral direction is preferably in a range of 10 to 50 mm and more preferably in a range of 15 to 40 mm. The height of the absorbent sheet body is preferably in a range of 3 to 30 mm in case of considering the content of an absorbent body having an appropriate absorption capacity, more preferably in a range of 10 to 20 mm.

In the "absorbent sheet body", the structure for containing the absorbent body in a cover sheet is not particularly limited if the absorbent body is enclosed so that the absorbent body does not separate away. The "enclosed type" structure where the cover sheet surrounds the absorbent body in a way to envelop the whole thereof, "joint type" structure where two cover sheets are disposed on the upper face and the lower face to bond both across the peripheral edge of the absorbent body, or others can be adopted properly.

As the "cover sheet" is in contact directly with the skin of the wearer, soft and liquid permeable ones that do not deteriorate the wearing feeling are used. For example, it can be selected from fiber sheet, porous fiber sheet, porous foam film, and so on. Particularly, it is preferable to use a bicomponent fiber having a PE/PP sheath-core structure subjected to a hydrophilic treatment with 2.2 dtex and formed into a through air sheet by a specific weight per unit of 25 g/m$^2$. It should be appreciated that, in case of adopting the "joint type" structure for the absorbent sheet body, it is also possible to use a liquid permeable material for the body side face and a liquid impermeable for the opposite body side face to body side face.

The shape of the "absorbent body" is not particularly limited and any shape making its cross section form planer, circular, square, triangular, cylindrical or hollow and so on can be adopted. The maximal height dimension is preferably in a range of 3 to 30 mm and more preferable in a range of 10 to 20 mm. It should be appreciated that, an absorbent sheet body of excellent absorption efficiency and wearability can be formed, by making the central portion of the absorbent body to have a slightly protruding central portion, which is thicker than the end portion.

The length dimension in the longitudinal direction of the junction sheet body may be equivalent to the full length in the longitudinal direction of the absorbent sheet body 2; however, it may be a dimension shorter than that of the absorbent sheet body, provided it has a length dimension equal or superior to two thirds at least in respect to the absorbent sheet body, considering the area for applying adhesive. The length dimension in the lateral direction is preferably in a range of 5 to 50 mm and more preferably in a range of 10 to 40 mm.

The "adhesive" to be applied to the opposite body side face to body side face of the junction sheet body is desirably selected from hot melts comprising mainly synthetic rubber such as SBS (styrene butadiene styrene block copolymer), SIS (styrene isoprene styrene block copolymer) or the like. Such adhesive is applied substantially all over the opposite body side face to body side face, in a planer, linear, dot or spiral pattern.

The absorbent article according to the present invention can be used largely for the hygienic article for absorbing body fluid such as postpartum napkin, post-operation napkin or the like, other than the sanitary napkin.

(2) The auxiliary pad for attaching to an absorbent article according to (1) wherein said linkage stem body is attached so as to be positioned substantially in the middle of said auxiliary pad for attaching to an absorbent article.

In the auxiliary pad for attaching to the absorbent article according to the present invention, the linkage stem body is attached to extend in the longitudinal direction, substantially in the middle of the lateral direction of the absorbent sheet body. Consequently, the absorbent sheet body is not inclined to the right or left during the fitting and supported in a stable state. Therefore, the absorbent sheet body can maintain a satisfactory contact state in respect to the inside of the thigh of the wearer, even if the absorbent article slips off in respect to the body of the wearer.

(3) The auxiliary pad for attaching to an absorbent article according to (1) or (2), wherein a height dimension of said linkage stem body ranges from 1 to 15 mm and, more preferably from 3 to 10 mm.

In such auxiliary pad for attaching to the absorbent article according to the present invention, the height dimension of the linkage stem body ranges from 1 to 15 mm. If the height dimension of the linkage stem body is shorter than 1 mm, the absorbent sheet body will follow the displacement of the absorbent article, turning into the same result as the case where the absorbent sheet body is attached adhesively as the aforementioned example of the prior art. On the other hand, if it is longer than 15 mm, it is difficult for the linkage stem body to support the absorbent sheet body all the way maintaining somewhat its form, and it can be bent easily, and it is also feared that the wearing feeling be deteriorated.

For this point, according to the present invention, even when the phase amount of the absorbent article in respect to the absorbent sheet body turns to be too large, the leakage of body fluid can be reduced further, as the state of secure contact of the absorbent sheet body to the inside of the thigh of the wearer can be maintained.

(4) The auxiliary pad for attaching to an absorbent article according to any one of (1) to (3), wherein said linkage stem body includes an elastic flexible member.

According to such auxiliary pad for attaching to the absorbent article of the present invention, as the linkage stem body contains an elastic flexible member, it becomes possible to have a convenient bending resistance.

Consequently, it is easy to return to the original shape at the moment of fitting, even if the linkage stem body deforms along with the displacement of the absorbent article.

As for the "elastic flexible member" that can be used in the present invention, those of band shape and string shape obtained from films comprising mainly synthetic rubbers such as SEBS (styrene ethylene butadiene styrene block copolymer), SIS (styrene isoprene styrene block copolymer), polyurethane, SEPS (styrene ethylene propylene styrene block copolymer) or the like, nonwoven fabric or natural rubber can be used.

The attachment area of the elastic flexible member in the linkage stem body may be designed to have a length equivalent to the linkage stem body; however, the range may be shorter than the linkage stem body, provided that an attachment length equal or superior to 50% is secured at least in the linkage stem body. The deformation restitution function as mentioned above can be secured by attaching the elastic flexible member in such a range.

It should be appreciated that the elastic flexible member is elongated by 1.1 to 1.5 times and fixed, and the stress at such moment of elongation is preferably 300 to 1000 mN. The stress of the elastic flexible member can be confirmed by setting the elastic flexible member on a tensilon tensile test machine with a chuck interval of 100 mm, pulling by a rate of 100 mm/min and reading the load when the elongation percentage is attained. The elastic flexible member can be fixed by applying adhesive on the surface of the elastic flexible member or the inner face side of the linkage stem body by means of coater or fog-like, net-like or omega-like spray, applying nip pressure and adhering one the other. The linkage stem body is prevented from generating an excessive deformation, by using elongation percentage, stress and fixing method mentioned above.

(5) The auxiliary pad for attaching to an absorbent article according to any one of (1) to (4), wherein said linkage stem body has a linkage sheet.

According to such auxiliary pad for the absorbent article of the present invention, the linkage stem body is formed by overlaying a single or a plurality of fiber-like linkage sheets. In short, according to the present invention, as the linkage stem body and the cover sheet are made of different sheets, a linkage sheet of a material appropriate for the linkage stem body can be selected conveniently, independently of the cover sheet.

As for the linkage sheet that can be used in the present invention, cylindrical, square, planer or laminated fiber sheet or foam sheet can be used. These sheets are preferably submitted to the hydrophilic treatment so that they can function as absorbing material.

As for fiber sheet, those selected from fibers of 1.1 to 3.3 dtex in size having a sheath-core structure of, for instance, PE/PP, PP/PET or others and, at the same time, crimped two-dimensionally or in a crimp shape in three dimensions. Especially, one made by a manufacturing method excellent in bulky and not imparting a stiff feeling, and more particularly nonwoven fabric formed by the through air method is preferable.

Non-woven sheet is used solely or overlaid and adjusted to have a volume of 1 to 15 mm. For instance, PE/PET fiber having a size of 2.2 dtex is made into a sheet of the order of 2.2 mm in volume by a specific weight per unit of 50 g/m$^2$ by the through air method, and a linkage sheet of about 10 mm can be formed by stacking five sheets through an adhesive.

As for foam sheet, one selected from closed cell or open cell sheets made by foaming a mixture of PE and EVA, SEBS (styrene ethylene butadiene styrene block copolymer) or polyurethane or other resin by a ratio of 10 to 30 times. More particularly, the linkage sheet can be obtained as a linkage stem body of about 12 mm, by laminating three sheets of the order of 4.2 mm in volume made by foaming the mixture of PE and EVA by 15 times, by intermediate of adhesive.

In the present invention, the linkage stem body can be composed by overlaying a plurality of linkage sheets so that the face portion comes into contact with the absorbent sheet body. In case of adopting such composition, a fine adjustment of the rigidity of the linkage stem body is made possible, compared to a case where the linkage stem body is composed by positioning a single sheet body vertically to the absorbent sheet body.

(6) The auxiliary pad for attaching to an absorbent article according to any one of (1) to (5), wherein said absorbent sheet body has a plurality of layers, and at least one of them is an elastic recovery sheet.

According to such auxiliary pad for the absorbent article of the present invention, the absorbent sheet body contains an elastic recovery sheet. Therefore, after fitting the auxiliary pad according to the present invention, even when inclination, flexion, distortion or other deformation is generated in the absorbent sheet body in contact with the body side according to the action of the wearer, the absorbent sheet body returns easily to the original shape at the moment of fitting. Such composition allows the absorbent sheet body to maintain a stable contact state in respect to the crotch and a further improved fitness, without deteriorating the wearing feeling. Especially, in case when the absorbent body is thinning, the wearer may have a fear of leakage; however, according to the present invention, the thickness can be restituted to the order of relieving the wearer of her anxiety.

The "elastic recovery sheet" has a measured value by JIS L-1018, cantilever A method in a range of 20 mm to 100 mm and more preferably in a range of 30 mm to 70 mm. By doing so, the fitness can be maintained, without deteriorating the wearing feeling.

The absorbent body and the elastic recovery sheet may simply be overlaid, but they may further be bent or wound up cylindrically. It should be appreciated that, in case of containing fiber crimped in a coil-shape into the absorbent sheet body, the compression restitution ability of the sheet can further be improved.

(7) The auxiliary pad for attaching to an absorbent article according to (6), wherein said absorbent sheet body has a convex portion of a gable-roof shape formed by bending.

According to such auxiliary pad for attaching to an absorbent article of the present invention, the absorbent sheet body is bent into a gable roof shape in a way to form a peak portion on the body side. Therefore, the absorbent sheet body can be brought into an adhesive contact with concave portion in the inside of the thigh of the wearer, such as space between the haunches. Especially, body fluid flowing from the crevasse of the haunches along the back can be prevented effectively from leaking backward. It should be appreciated that the absorbent sheet body can be made to touch softly the body of the wearer, by making the peak portion of the convex portion into a round bend.

(8) The auxiliary pad for attaching to an absorbent article according to (7), further comprising a restriction sheet for restricting development of a bent portion attached to both base portions in the longitudinal direction of said convex portion.

According to such auxiliary pad for the absorbent article of the present invention, a restriction sheet is attached, in a way to extend from one bottom portion to the other bottom portion, in the longitudinal direction of the convex portion. Therefore, the absorbent sheet body bent before fitting is prevented from unfolding, and the wearer can maintain the shape of the convex portion without paying attention especially, until wearing the auxiliary pad according to the present invention. In addition, during the wearing, the convex portion is prevented from deforming into a flat shape, by the compression due to the wearing pressure, and its shape can be maintained easily even if the usage is prolonged.

The restriction sheet is preferably of the length range at least equal or superior to one fifth, in respect to the full length of the absorbent body. By adopting such dimension, it becomes possible to prevent securely the bent absorbent sheet body from unfolding.

As "restriction sheet", either elastic sheet or inelastic sheet can be used, but it is preferable to adopt an elastic sheet. The elastic sheet includes those of band shape and string shape obtained from films comprising mainly synthetic rubbers such as SEBS (styrene ethylene butadiene styrene block copolymer), SIS (styrene isoprene styrene block copolymer), polyurethane, SEPS (styrene ethylene propylene styrene block copolymer) or the like, nonwoven fabric or natural rubber. Such elastic sheet is used by elongating by 1.1 to 1.8 times in the lateral direction. In this case, the stress of the elastic sheet is preferably 2 mN to 8 mN. The stress can be confirmed by setting the elastic flexible material on the tensilon tensile test machine with a chuck interval of 100 mm, pulling by a rate of 100 mm/min and reading the load when the elongation percentage is attained. By adopting the structure, the form can be restituted rapidly along with the flexible behavior of the elastic material even when the wearing pressure is imposed.

(9) The auxiliary pad for attaching to an absorbent article according to any one of (1) to (8), wherein the auxiliary pad for attaching to an absorbent article is an auxiliary pad for incontinence of urine.

According to such auxiliary pad for attaching to an absorbent article of the present invention, it can be used as absorbent pad for incontinence. In short, as the ostium vaginae discharging menstrual blood and the urethral meatus for discharging urine are both found between interlabia, not only menstrual blood but also incontinence of urine can be absorbed, in case of using the auxiliary pad for the absorbent article according to the present invention pinched between interlabia.

Thus, according to the present invention, an absorbent pad effective for incontinence of urine, especially for a slight incontinence of urine can be obtained, as it can absorb urine between interlabia, especially near the urethral meatus.

(10) The auxiliary pad for attaching to an absorbent article according to any one of claims (1) to (8), wherein the auxiliary pad for attaching to an absorbent article is an auxiliary pad for absorbing a vaginal discharge.

According to such auxiliary pad for attaching to an absorbent article of the present invention, the auxiliary pad for the absorbent article can be used for absorbing the vaginal discharge. In short, as the auxiliary pad for attaching to an absorbent article according to the present invention is pinched between interlabia for use, it can absorb the discharge (vaginal discharge) other than menstrual blood from the ostium vaginae, so it can be used for this application (vaginal discharge absorption).

(11) A linkage stem body for connecting a general absorbent article, which can be provided for a general use for absorbing body fluid, to a special absorbent article, which has body fluid absorption capacity less than said general absorbent article, and which can be provided for use with the general absorbent article to function to supplement its body fluid absorption capacity, wherein the linkage stem body has such flexibility that it can prevent said general absorbent article and said special absorbent article from moving together.

As such, according to the present invention, the linkage stem body is not connected with a general absorbent article such as sanitary napkin, nor with a special absorbent article for helping the body fluid absorption capacity of the general absorbent article and, thus, is independent. Consequently, the wearer can select separately each of general absorbent article and special absorbent article, and combine them as she will, to obtain a hygienic article appropriate for her.

(12) A set of hygienic article, comprising: a general absorbent article, which can be provided for a general use for absorbing body fluid, a special absorbent article, which has body fluid absorption capacity less than said general absorbent article, and which can be provided for use with the general absorbent article to function to supplement its body fluid absorption capacity, and a linkage stem body for connecting said general absorbent article to said special absorbent article, wherein said general absorbent article and said special absorbent article are used respectively solely or in combination, and used appropriately in combination with said linkage stem body.

As such, according to the present invention, a generally used absorbent article such as sanitary napkin and a special absorbent article for enhancing the leakage prevention effect by helping its body fluid absorption function constitute a set. Consequently, the wearer can use the set of hygienic article according to the present invention, in function of her body fluid flow quantity, or, enjoy a variety of combinations in accordance with her feeling or physical condition of the day. For example, a female wearer can use only the general absorbent article similarly as an ordinary sanitary napkin, in accordance with the quantity of menstrual blood, or as a sanitary article of enhanced leakage prevention effect by combining conveniently with a special absorbent body and so on.

Thus, the set of hygienic article according to the present invention can be used as hygienic article, relieved from functional restrictions of the ready-made absorbent product and having a versatile function.

In addition, the wearer, if only she has a set of hygienic article according to the present invention, she can build up a most appropriate absorbent article as necessary. This will relieve the wearer from a troublesome preliminary choice of an appropriate absorbent article before going out, and have an effect of enlarging the area of activity or the activity of the wearer.

DETAILED DESCRIPTION OF THE PREFERRED EMBODIMENT

Next, embodiments of the auxiliary pad for the absorbent article of the present invention shall be described referring to drawings.

Figure 1:
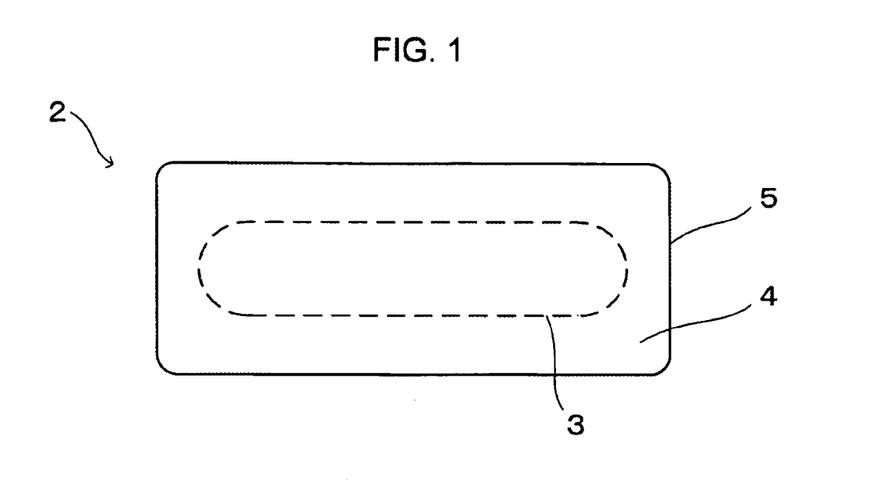
FIG. 1 is a schematic top view for illustrating an auxiliary pad for the absorbent article in the present embodiment.
Figure 2:
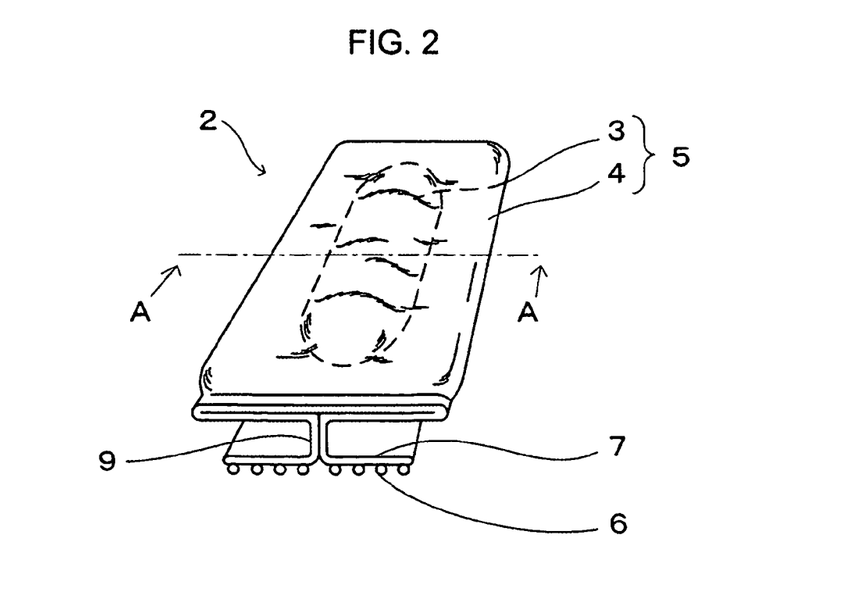
FIG. 2 is a schematic perspective view for illustrating the auxiliary pad for the absorbent article in the present embodiment.
Figure 3:
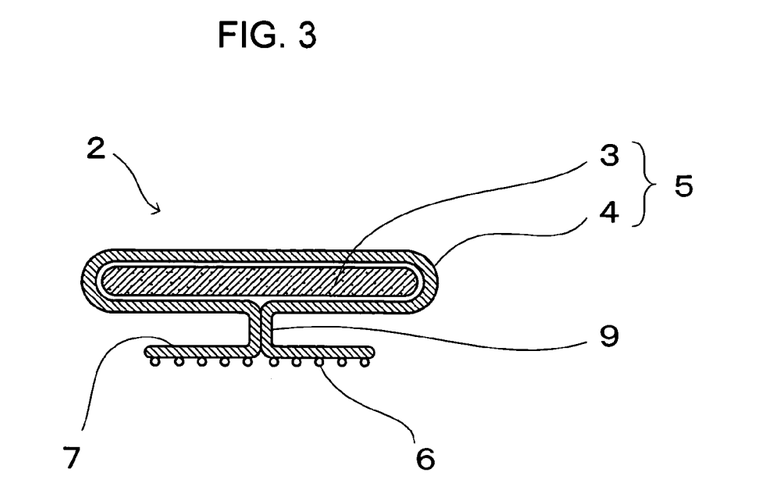
FIG. 3 is a cross sectional view along A—A in FIG. 2 showing an absorbent body of the auxiliary pad for the absorbent article in the present embodiment.
Figure 4:
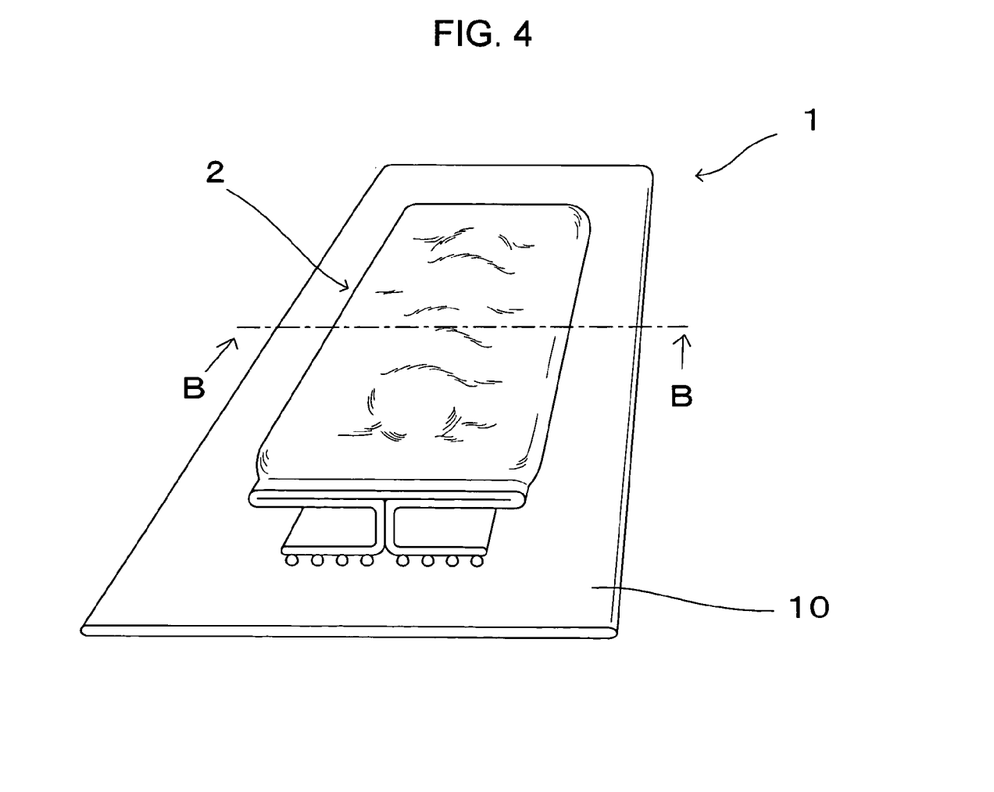
FIG. 4 is a schematic perspective view for showing a state where the auxiliary pad for the absorbent article is attached to a sanitary napkin in the present embodiment.
Figure 5:
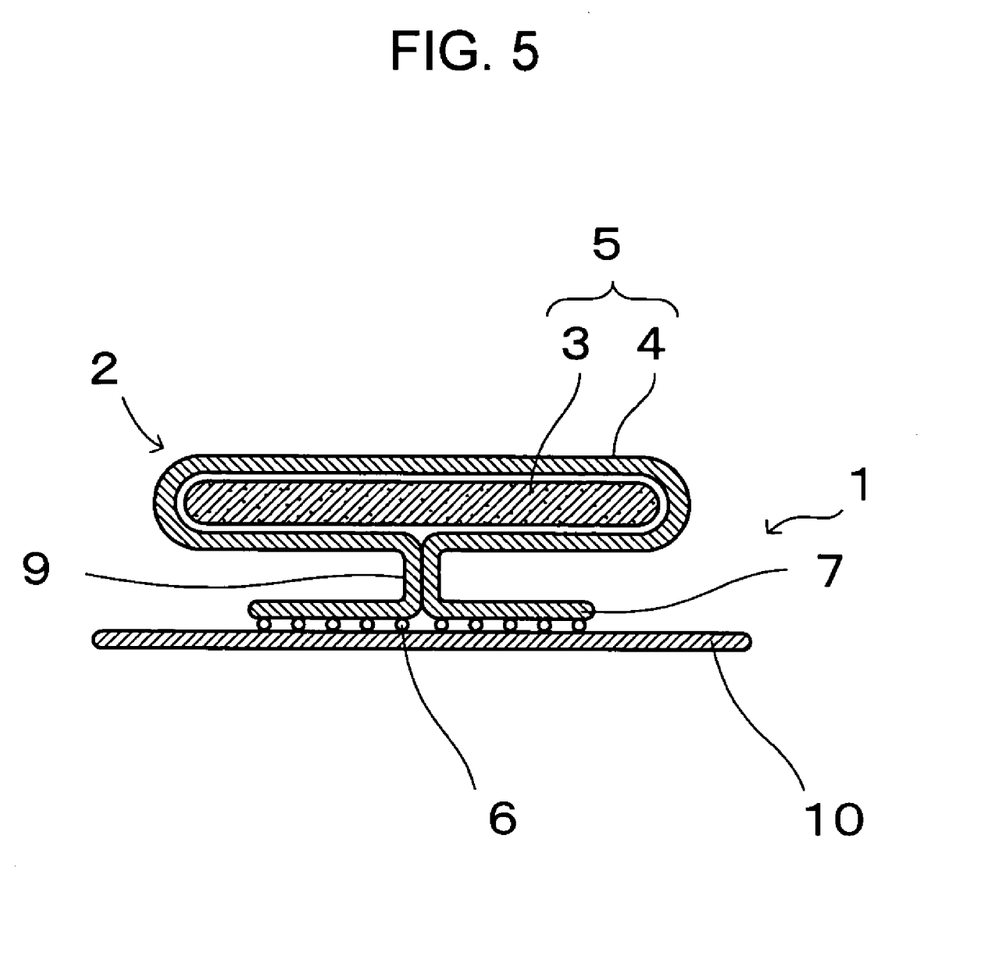
FIG. 5 is a cross sectional view along B—B in FIG. 4 showing the state where the auxiliary pad for the absorbent article of the present embodiment is attached to the sanitary napkin.

FIG. 1 is a schematic top view for illustrating an auxiliary pad for the absorbent article 2 in the present embodiment; FIG. 2 is a schematic perspective view for illustrating the auxiliary pad for the absorbent article 2 in the present embodiment; FIG. 3 is a cross sectional view along A—A in FIG. 2 showing an absorbent body of the auxiliary pad for the absorbent article 2 in the present embodiment; FIG. 4 is a schematic perspective view for showing a state where the auxiliary pad for the absorbent article 2 is attached to a sanitary napkin 10 in the present embodiment; FIG. 5 is a cross sectional view along B—B in FIG. 4 showing the state where the auxiliary pad for the absorbent article 2 of the present embodiment is attached to the sanitary napkin 10.

The auxiliary pad for the absorbent article 2 of the present embodiment comprises an absorbent sheet body 5, a junction sheet body 7 for adhesion with a sanitary napkin 10, and a linkage stem body 9 for linking the absorbent sheet body 5 and the sanitary napkin 10. When the auxiliary pad for the absorbent article 2 is viewed from the body side, as shown in FIG. 1, only the absorbent sheet body 5 can be seen. As shown in FIG. 2, a flat junction sheet body 7 is provided on the absorbent sheet body 5, in parallel to the same. For the junction sheet body 7, an adhesive 6 is applied to its opposite body side face to body side face, for attaching to a not shown sanitary napkin. The junction sheet body 7 and the absorbent sheet body 5 are linked by the linkage stem body 9.

The linkage stem body 9 has a flexibility that can prevent the auxiliary pad for the absorbent article 2 and the sanitary napkin from moving together. Therefore, when a wearer using the auxiliary pad for the absorbent article 2 attached to a sanitary napkin moves around, even if the sanitary napkin slips off relatively in respect to the labia of the wearer, only the linkage stem body 9 deforms with its flexibility, and the absorbent sheet body 5 would not slip off following the shift of the sanitary napkin. Namely, as for the auxiliary pad for the absorbent article 2 according to the present invention, even if a gap is generated between the sanitary napkin and the labia of the wearer, only a phase shift generates in respect to the sanitary napkin, and the absorbent sheet body 5 is kept in a state of close contact with the labia.

As shown in FIG. 3, and the absorbent sheet body 5 comprises an absorbent body 3 substantially longitudinal for absorbing body fluid, and a cover sheet 4 for covering the absorbent body 3, and a linkage stem body 9 for binding the absorbent sheet body 5 and a junction sheet body 7 is provided in a way to extend along the longitudinal direction in a substantially middle portion in the lateral direction of the absorbent sheet body 5. Consequently, the absorbent sheet body 5 is supported in a stable state in respect to a sanitary napkin which is not shown here, and can maintain an appropriate contact state with the crotch of the wearer, even if the sanitary napkin slips off right or left during the wearing.

As shown in FIG. 3, the absorbent body 3 is covered with a single cover sheet 4 in a way to envelop the whole absorbent body 3 by turning from the body face side to the opposite face side to body face through both right and left side face. Back faces of both right and left end portions of the cover sheet 4 are bonded in a state stuck together mutual pasting on the back side of the absorbent body 3, and the cover sheet extends downward as it is. Then, a linkage stem body 9 is formed in such extension portion.

The cover sheet 4 where the linkage stem body 9 is formed, extends both right and left edge end portions thereof flatly to both right and left side respectively, and an adhesive 6 applied to the opposite body side face to body side face of that portion extending flatly. A junction sheet body 7 is formed in such flat portion.

As described above, in the auxiliary pad for the absorbent article 2 according to the present embodiment, the cover sheet 4 serves as linkage stem body 9 and junction sheet body 7 at the same time, and they turn up to be formed integrally. As a result, the connection strength is improved considerably, compared to a case where they are manufactured separately and then adhered.

Then, the auxiliary pad for the absorbent article 2 having the structure as mentioned above is pasted to a sanitary napkin 10 and turns up to be used as sanitary article 1.

For using the auxiliary pad for the absorbent article 2 according to the present embodiment, it is preferable to paste approximately to the middle portion of the sanitary napkin 10. Whereby, even if the sanitary napkin 10 slips off laterally to the right or left in respect to the body of the wearer, the absorbent sheet body 5 adhered to the crotch of the wearer can be maintained easily in the crotch.

As shown in FIG. 5, the auxiliary pad for the absorbent article 2 is used by attaching to the sanitary napkin 10 through an adhesive 6 on the back of the junction sheet body 7. In this case, viewed from the body side face, the absorbent sheet body 5 and the sanitary napkin 10 are made to overlay, but they are not connected directly, because a linkage stem body 9 is interposed between them. Consequently, even if the sanitary napkin 10 moves in the vertical or lateral direction, the absorbent sheet body 5 can be adhered to the crotch of the wearer continuously.

Figure 6:
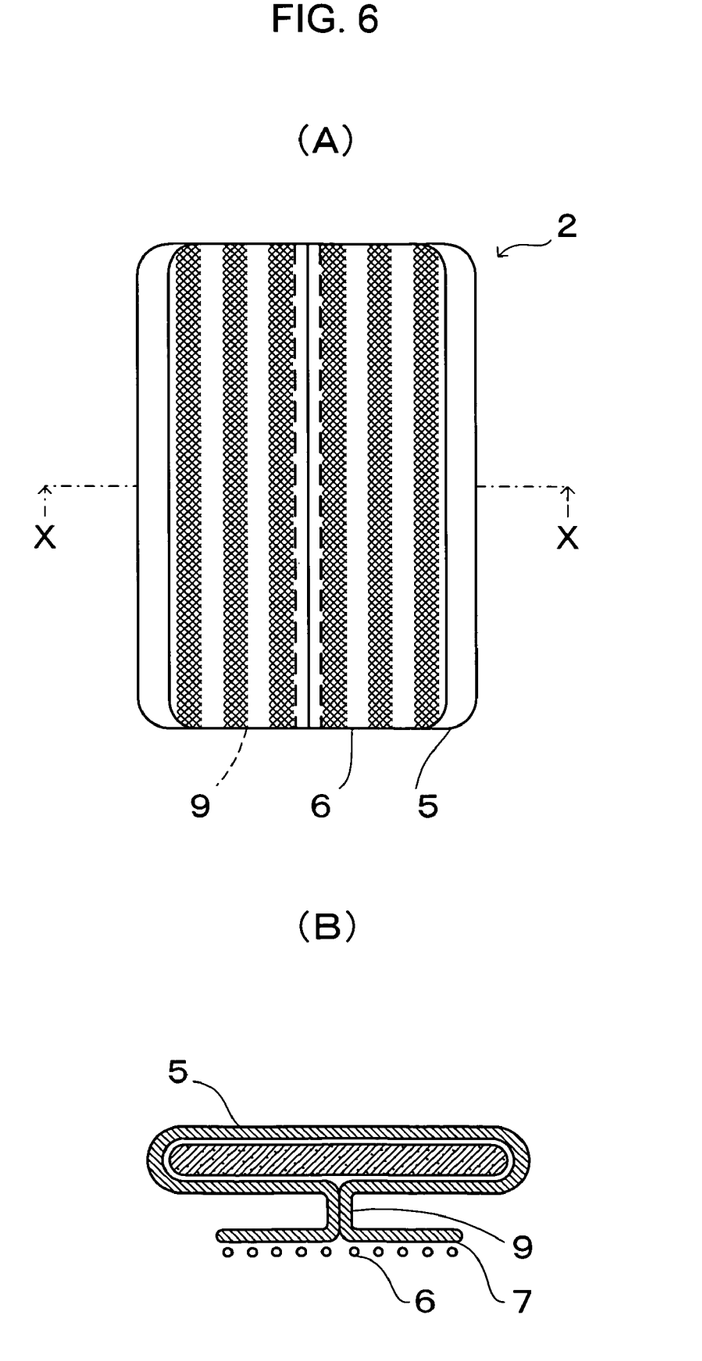
FIG. 6 represents the auxiliary pad for the absorbent article according to the present embodiment viewed from the opposite side to the body side and the cross sectional view thereof.
Figure 7:
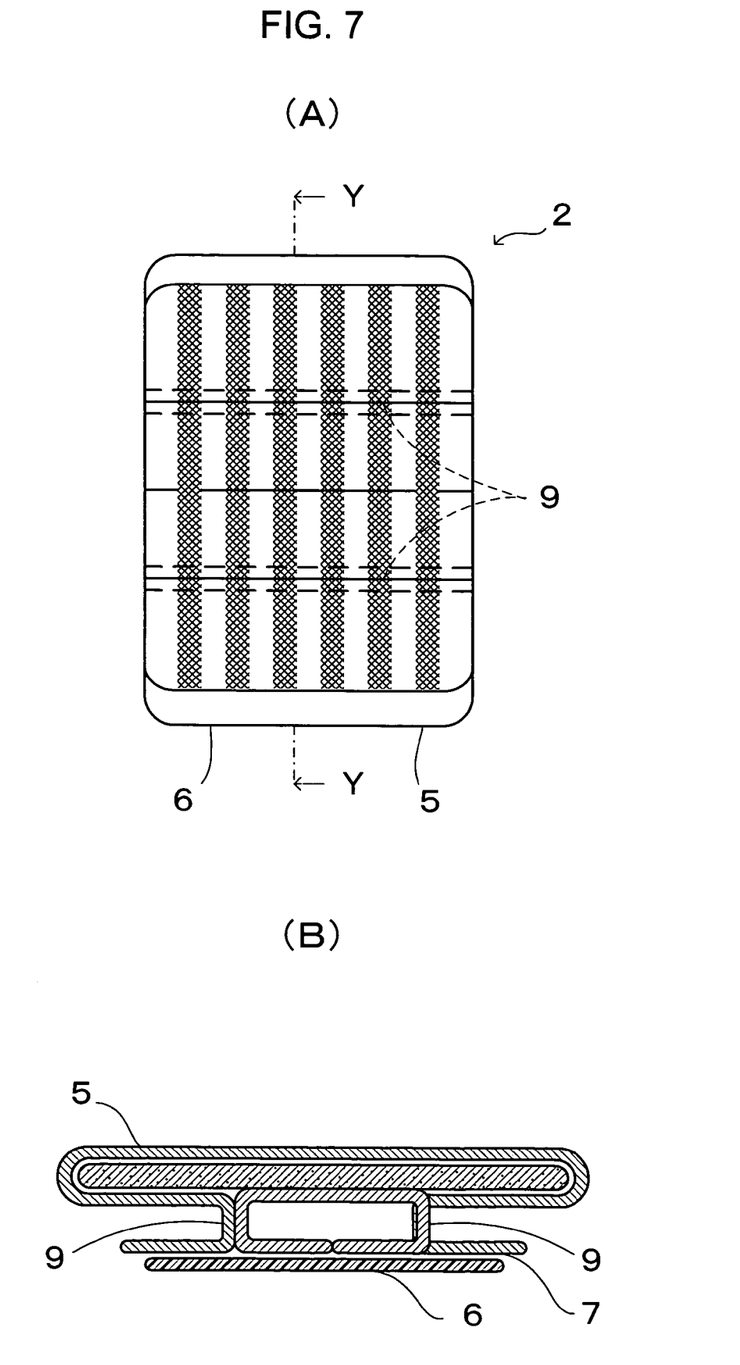
FIG. 7 represents an auxiliary pad for the absorbent article according to another embodiment viewed from the opposite side to the body side and the cross sectional view thereof.

Now, the attachment situation of the linkage stem body 9 shall be described. FIG. 6 represents the auxiliary pad for the absorbent article 2 according to the present embodiment viewed from the opposite side to the body side (A) and the cross sectional view thereof (B). FIG. 7 represents an auxiliary pad for the absorbent article 2 according to another embodiment viewed from the opposite side to the body side (A) and the cross sectional view thereof (B).

The auxiliary pad for the absorbent article 2 according to the present embodiment viewed from the opposite side to the body side, as shown in FIG. 6(A) has the linkage stem body 9 formed continuously in the longitudinal direction. There, as shown in FIG. 6(B), cross sectional view along X—X, the quantity of linkage stem body 9 is one. The linkage stem body 9 can be attached in a different direction, and can also be provided in plurality as necessary. For instance, as shown in FIG. 7(A), it is possible to position the linkage stem body 9 vertical to the absorbent sheet body 5 and, as shown in FIG. 7(B), two linkage stem bodies 9 can be disposed. By doing so, the tensile strength of the linkage stem body 9 can be enhanced. According to such structure, the linkage stem body 9 can cope with an excessive deformation, all the way securing its flexibility.

[Composition of Linkage Stem Body]

The linkage stem body 9 can be formed by various composition methods that will be described in detail below.

Figure 8:
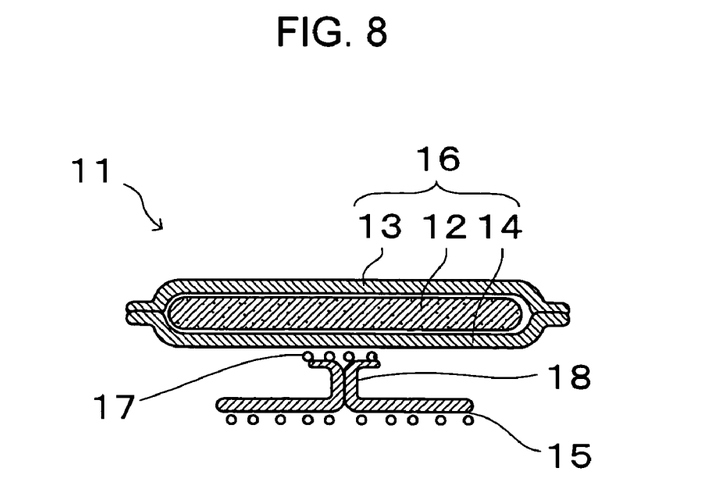
FIG. 8 shows an example of linkage stem body of the present embodiment, wherein the linkage stem body is attached to an absorbent sheet body formed by pinching and covering an absorbent body with a cover sheet.

In the auxiliary pad for the absorbent article 11 shown in FIG. 8, an absorbent sheet body 16 is formed integrally, by binding an absorbent body 12 in a way to pinch with a cover sheet 13 positioned on the body side thereof and a cover sheet 14 positioned on the opposite side to the body side. Then, a linkage stem body 18 is disposed on the opposite side to the body side of the absorbent sheet body 16. The absorbent body 12 and the cover sheets 13 and 14 are bonded with a so-called pressure sensitive hot melt applied all over the surface, linearly, helically or in fiber shape. In addition, the cover sheet 14 and the linkage stem body 18 are adhered by an adhesive 17 made of hot melt. According to such structure, as the absorbent sheet body 16, linkage stem body 18 and junction sheet body 15 can be manufactured in parallel, it becomes possible to combine the cover sheets 13 and 14 and the linkage stem body 18, respectively with a suitable and different material.

Figure 9:
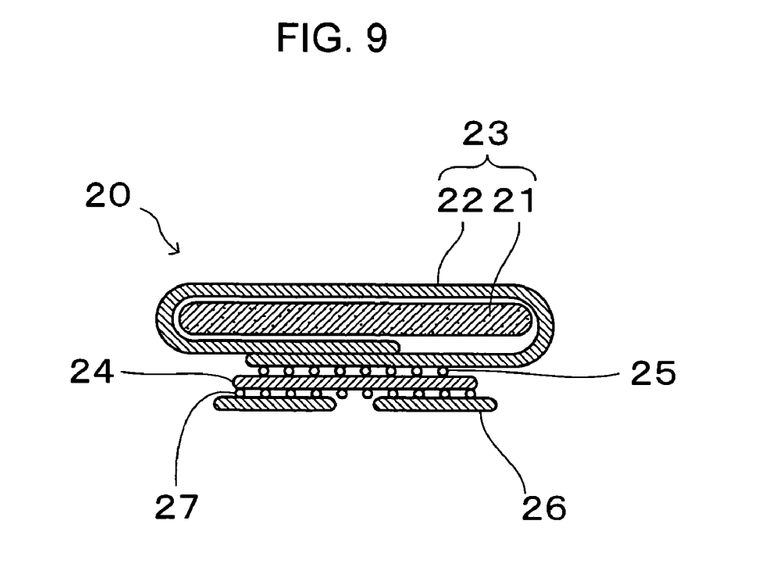
FIG. 9 shows an example of linkage stem body of the present embodiment, wherein the linkage stem body is composed of a linkage sheet.

In the auxiliary pad for the absorbent article 20 shown in FIG. 9, an absorbent sheet body 23 is composed by surrounding an absorbent body 21 totally with a cover sheet 22 and binding so that both end portions of the cover sheet 22 are overlaid up and down on the opposite side to the body side of the absorbent body 21. There, a plate-like linkage sheet 24 is bonded through an adhesive 25, in a portion where the cover sheet 22 is overlaid each other. A junction sheet body 26 is made of nonwoven fabric, film, laminated paper and so on and affixed to the aforementioned linkage sheet 24 by an adhesive 27.

Figure 10:
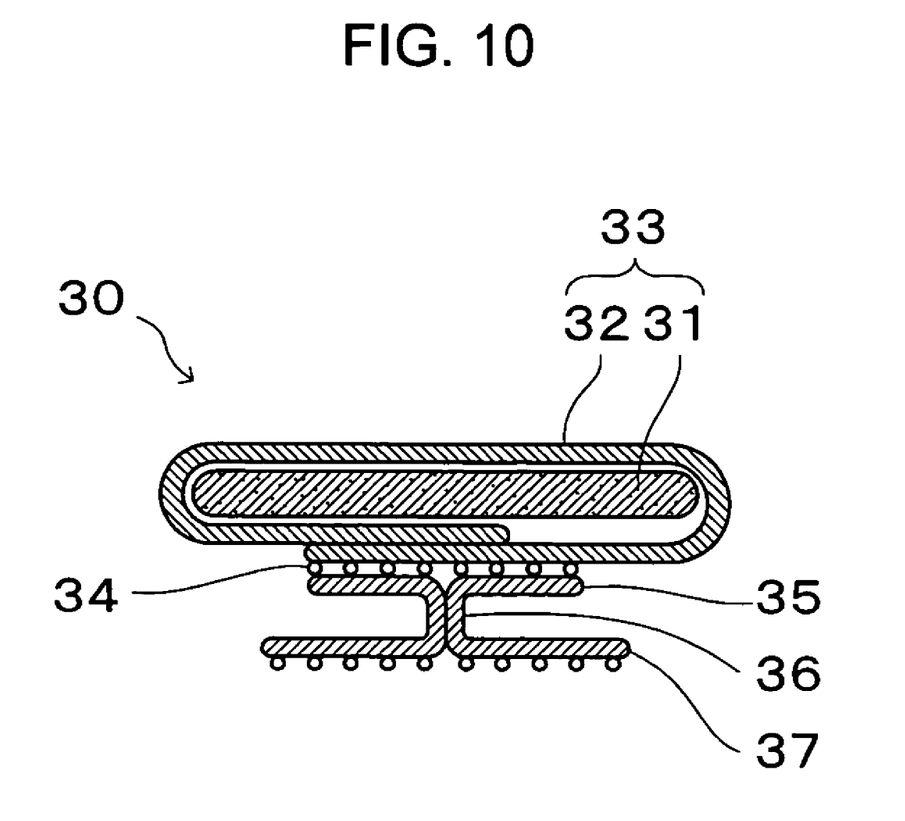
FIG. 10 shows an example of linkage stem body of the present embodiment, wherein the linkage stem body is attached to a portion where both ends of a cover sheet are overlaid each other on the back side of an absorbent body.

In the auxiliary pad for the absorbent article 30 shown in FIG. 10, an absorbent sheet body 33 is formed, by making a cover sheet 32 covering an absorbent body 31 to surround the absorbent body 31 so that both end portions thereof overlay on the back face side of absorbent body 31. There, a linkage stem body 36 is provided with an adhesive application area 35 for joining with an absorbent sheet body 33. The linkage stem body 36 and the absorbent sheet body 33 are bonded by applying an adhesive 34 to the adhesive application area 35.

The adhesive application area 35, linkage stem body 36 and junction sheet body 37 are formed by bending a series of two sheets. The linkage stem body 36 is formed in a portion where these two sheets are pasted together, and the adhesive application area 35 on the body side and the junction sheet body 37 on the opposite side to the body side, respectively are formed, in a portion where they are not pasted together.

The adhesive application area 35 is pasted to the absorbent sheet body 33, in a portion where the thickness dimension is increased by the mutual overlay of the cover sheet 32. By doing so, the linkage area of the absorbent sheet body 33 and the linkage stem body 36 is stronger than the aforementioned embodiment of FIG. 8, and the risk of damage is reduced.

Figure 11:
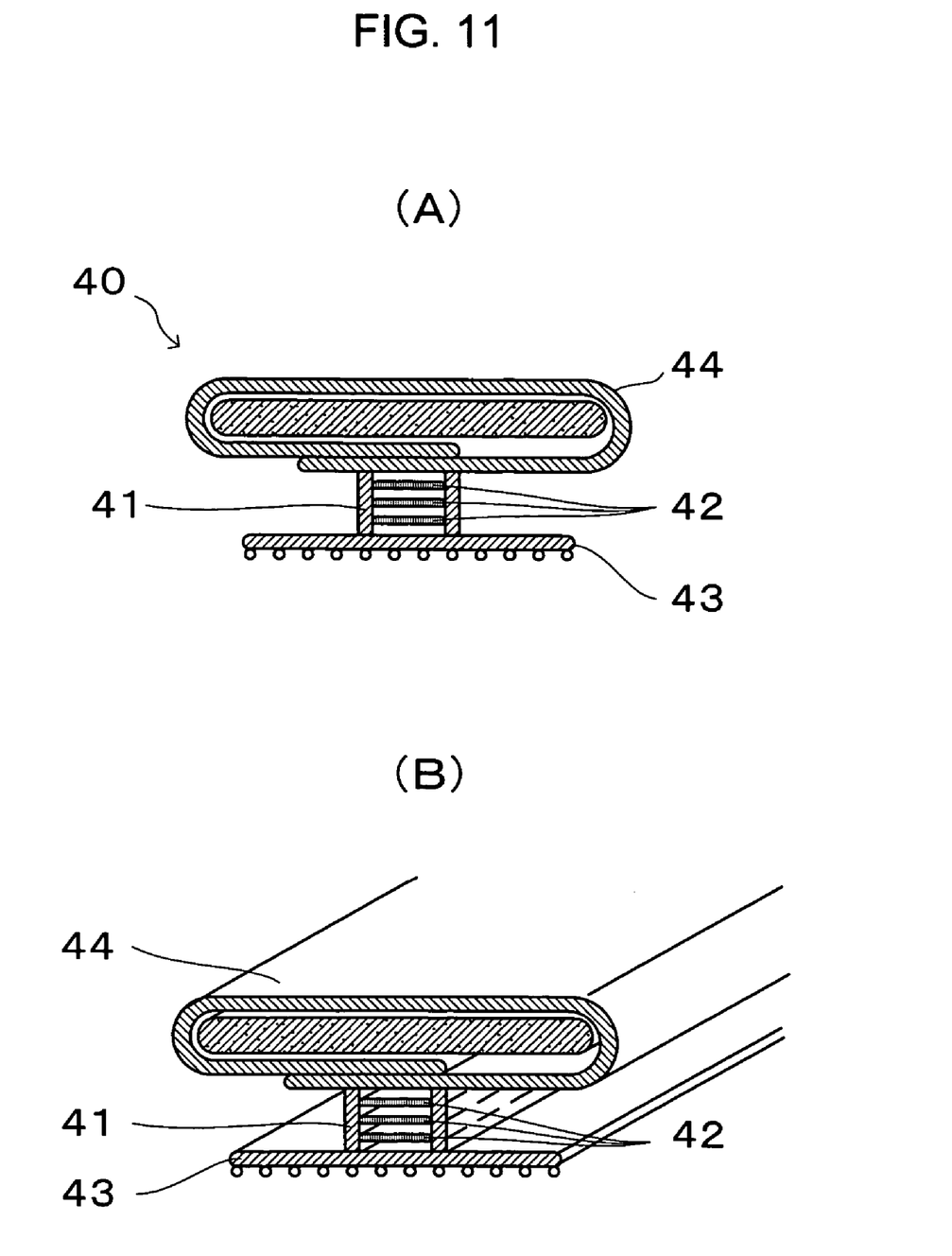
FIG. 11 is an illustrative drawing for illustrating a case wherein an elastic flexible member is attached to a linkage stem body, in the present embodiment.

In the auxiliary pad for the absorbent article shown in FIG. 11(A), an elastic flexible member 42 is provided in a linkage stem body 41. Consequently, even when a sanitary napkin (not shown) attached through a junction sheet body 43 moves right and left or back and forward in respect to the body of the wearer, the linkage stem body 41 can compensate the position appropriately, against the displacement of the sanitary napkin, according to the action of the wearer. In such composition, the restriction against the movement of the absorbent sheet body 44 along with the displacement of the sanitary napkin, enhancing further the leakage prevention function. It should be noted that the junction sheet body 43 is arranged parallel to the absorbent sheet body 44, as it is obvious from FIG. 11(B), perspective view of FIG. 11(A).

[Composition of Absorbent Sheet Body]

Next, the composition of absorbent sheet body shall be described.

Figure 12:
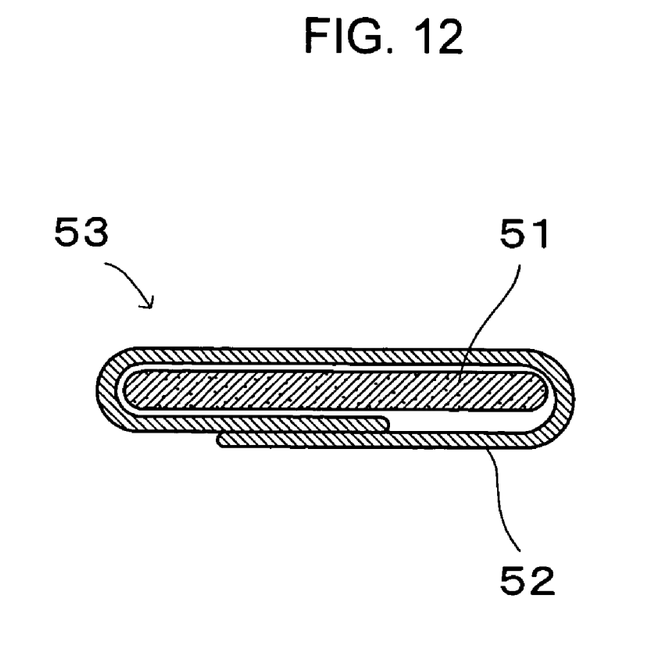
FIG. 12 shows an example of absorbent sheet body of the present invention, wherein an absorbent body is covered with a cover sheet.

FIG. 12 is an illustrative view for describing an absorbent sheet body 53 covering an absorbent body 51 with a cover sheet 52. In the present embodiment, a material or composite material known as composition material of absorbent body for absorbent products of the prior art is used for the absorbent body 51. For instance, fluff pulp, granular, fiber or foam-like super absorbent polymer, regenerated cellulose fiber, natural cellulose fiber, airlaid pulp, tissue, synthetic fiber and so on can be used solely or in mixture. Especially, in order to have a wet strength that would not damage the absorbent material during the wearing, more particularly, an absorbent material obtained by mixing a polymer absorbent material of sodium polyacrylate to which fluff pulp is laminated by a specific weight per unit of 100 g/m² by a ratio of 30 g/m², binder is sprayed before forming into a sheet, and laminating three sheets of airlaid absorbent material adjusted to 1.5 mm in height is preferable. Each airlaid absorbent material may also be formed by rolling in by several turns into a cylindrical shape.

Figure 13:
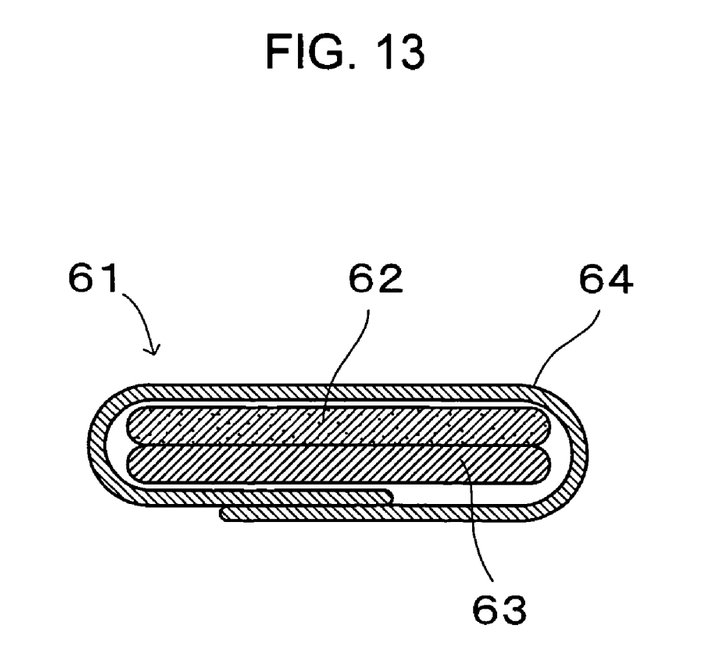
FIG. 13 shows an example of absorbent sheet body of the present invention, wherein an elastic recovery sheet is laid on the lower face side of an absorbent body.

FIG. 13 is an illustrative view for describing an absorbent sheet body 61 having a structure where an elastic recovery sheet 63 is overlaid on the lower face side of an absorbent body 62. According to the structure, the elastic recovery sheet 63 is overlaid on the opposite side to the body side of the absorbent body 62 for absorbing body fluid, and a cover sheet 64 surrounds the absorbent body 62 and the elastic recovery sheet 63, so as to cover them. Thus, an absorbent sheet body 61 includes two layers, of which one layer is the elastic recovery sheet 63; therefore, a force to return to the original shape against the deformation of the absorbent sheet body 61 is imparted to the same. As a result, compared to a case where it includes only the absorbent body as in the case of FIG. 12, a stable contact with the crotch or other areas can be maintained easily, even when the absorbent body 62 is bent, collapsed or otherwise deformed, and moreover, it becomes possible to maintain an enhanced fit.

Though, in FIG. 13, the absorbent sheet body 61 is shown to include two layers as mentioned above, of which one layer is the elastic recovery sheet 63, it is not limited to this, and for example, a structure where two absorbent bodies 62 are disposed, and the elastic recovery sheet 63 is sandwiched between them can also be adopted.

Figure 14:
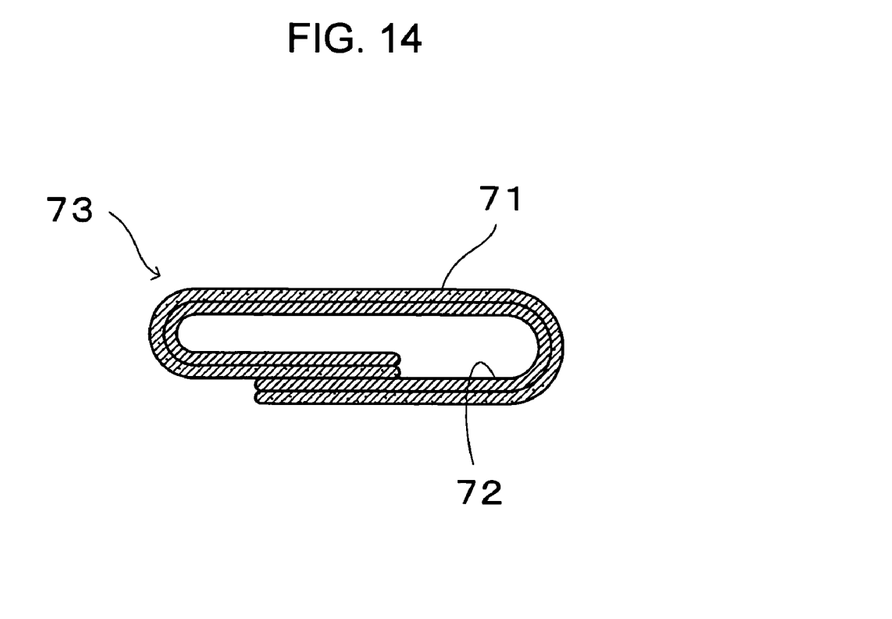
FIG. 14 shows an example of absorbent sheet body of the present invention, wherein an absorbent body and an elastic recovery sheet are overlaid in a plane and wound up cylindrically.

FIG. 14 is an illustrative view for describing an absorbent sheet body 73 composed by overlaying an absorbent body 71 and an elastic recovery sheet 72 flatly. According to the structure, the inside face of the absorbent body 71 and the face side of the elastic recovery sheet 72 are pasted together, so that the absorbent body 71 encapsulates the elastic recovery sheet 72. Consequently, it becomes possible to maintain the shape of the absorbent body 71 against the pressure to any portion of the absorbent sheet body 73, and the deformation of the absorbent sheet body 73 is much more reduced then the corresponding absorbent sheet body 61 shown in FIG. 13 against the pressure from the body side. It should be noted that the cover sheet is omitted in FIG. 14.

Figure 15:
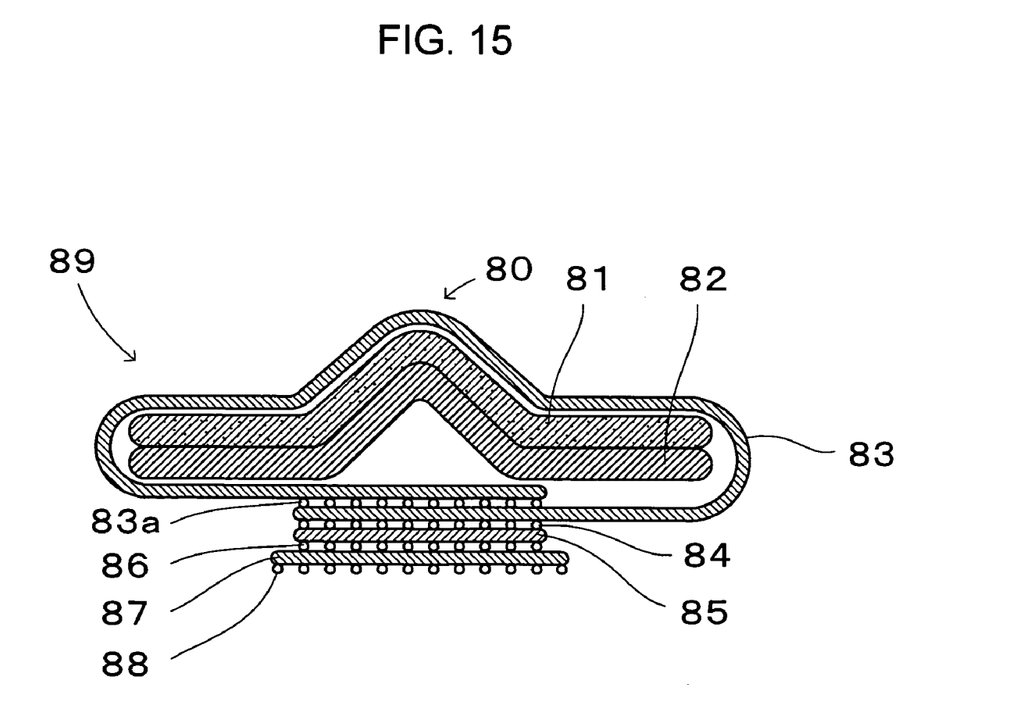
FIG. 15 shows an example of absorbent sheet body of the present invention, wherein the lower face of an absorbent body and the upper face of an elastic recovery sheet are overlaid, a cover sheet is extended on the bottom face side, the overlaid portion is affixed with adhesive and protruded in convex form toward the face applied to the skin.

FIG. 15 is an illustrative view for describing an absorbent sheet body 89, wherein a convex portion 80 is formed by folding an absorbent body 81 and an elastic recovery sheet 82, together with a cover sheet 83, at the middle portion in the lateral direction in the absorbent sheet body 89. According to the present embodiment, the gable roof-like convex portion 80 is formed toward the side applied to the skin, by overlaying the opposite side to the body side of the absorbent body 81 and the body side face of the elastic recovery sheet 82, folding with the cover sheet 83. The end portion of the cover sheet 83 is overlaid on the bottom face corresponding to the convex portion 80, and pasted with an adhesive 83a. A junction sheet 85 as linkage stem body is bonded with an adhesive 84, in a portion where the cover sheet 83 is overlaid, and the junction sheet 85 is bonded with a junction sheet body 87 by an adhesive 86.

On the lower face side of a protruding absorbent sheet body 89, in a portion corresponding to the convex portion 80, the junction sheet 85 as a linkage stem body and the junction sheet body 87 to which an adhesive 88 is applied are affixed by the adhesive 86. According to such structure, during the fitting, the wearer can bring easily the absorbent sheet body 89 across the surface into contact with a concave portion such as the bottom cleavage, where it is extremely effective to control the backward leakage.

Figure 16:
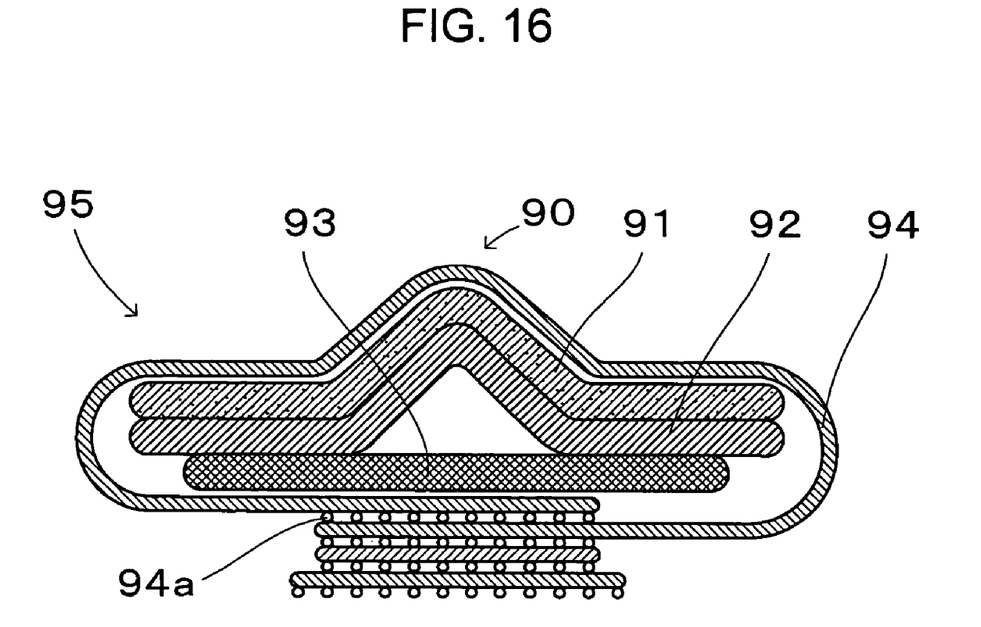
FIG. 16 shows an example of absorbent sheet body of the present invention, wherein a restriction sheet of protrusion structure for binding both side edges is interposed on an absorbent body and the bottom face side of an elastic recovery sheet pasted to the back face thereof.

FIG. 16 is an illustrative view for explaining an absorbent sheet body 95, wherein a restriction sheet 93 for binding both side edges of a protrusion structure is interposed on the bottom face side of a convex portion 90 of an absorbent body 91 and an elastic recovery sheet 92 pasted to the back face thereof. According to the present embodiment, the restriction sheet 93 is attached for binding both side edges of the convex portion 90, in a portion corresponding to the convex portion 90 of the absorbent body 91 and the elastic recovery sheet 92 pasted to the back face thereof. Then, a cover sheet 94 is disposed in a way to wrap the whole of absorbent body 91, elastic recovery sheet 92 and restriction sheet 93, end portions of the cover sheet 94 are overlaid, on the opposite body side face to the body side of the restriction sheet 93, and pasted with an adhesive 94a, forming an absorbent sheet body 95. According to such structure, the folded absorbent sheet body 95 and the elastic recovery sheet 92 are prevented from unfolding, and the shape keeping ability of the convex portion 90 is enhanced.

INDUSTRIAL APPLICABILITY

The auxiliary pad for the absorbent article according to the present invention described hereinabove, can prevent effectively body fluid from leaking by assisting body fluid absorption by an absorbent article, even if the absorbent article slips off in respect to the body of the wearer along with the action of the wearer.

Besides, a good fitness is sustained even when it is worn for a long time, and it can also serve as auxiliary for an absorbent article, which is convenient for carrying.

What is claimed is:

1. An auxiliary pad for attaching to an absorbent article, comprising:

an absorbent sheet body including an absorbent body for absorbing liquid and a single cover sheet for covering the absorbent body, a junction sheet body having an adhesive layer for attaching to the absorbent article, and a linkage stem body for linking said absorbent sheet body and the junction sheet body, wherein said absorbent sheet body has a plurality of layers, and at least one of said layers has an elastic recovery sheet, wherein the single cover sheet surrounds the plurality of layers and the elastic recovery sheet, and wherein said linkage stem body has such flexibility that it can prevent said absorbent sheet body and said absorbent article from moving together.

2. The auxiliary pad for attaching to an absorbent article according to claim 1, wherein said linkage stem body is attached so as to be positioned substantially in the middle of said auxiliary pad for attaching to an absorbent article.

3. The auxiliary pad for attaching to an absorbent article according to claim 1 or 2, wherein a. height dimension of said linkage stem body ranges from 1 to 15 mm.

4. The auxiliary pad for attaching to an absorbent article according to claim 1 or 2, wherein said linkage stem body includes an elastic flexible member.

5. The auxiliary pad for attaching to an absorbent article according to claim 1 or 2, wherein said linkage stem body has a linkage sheet.

6. The auxiliary pad for attaching to an absorbent article according to claim 1 or 2, wherein the absorbent sheet body has a convex portion having a gable-roof shape formed by bending.

7. The auxiliary pad for attaching to an absorbent article according to claim 6, further comprising a restriction sheet for restricting development of a bent portion attached to both base portions in the longitudinal direction of said convex portion.

8. The auxiliary pad for attaching to an absorbent article according to claim 1 or 2, wherein the auxiliary pad for attaching to an absorbent article is an auxiliary pad for incontinence of urine.

9. The auxiliary pad for attaching to an absorbent article according to any claim 1 or 2, wherein the auxiliary pad for attaching to an absorbent article is an auxiliary pad for absorbing a vaginal discharge.

10. A linkage stem body for connecting a general absorbent article, which can be provided for a general use for absorbing body fluid, to a special absorbent article, which has body fluid absorption capacity less than said general absorbent article, and which can be provided for use with the general absorbent article to function to supplement its body fluid absorption capacity, wherein the linkage stem body comprising:

a single cover sheet surrounding an absorbent body of the special absorbent article, the single cover sheet having a left end portion having a back face and a right end portion having a back face, the left and right end portions back faces being joined onto a back face side of the absorbent body; and an extending portion formed on a lower side of the linkage stem body.

11. A hygienic article, comprising:

a general absorbent article, provided for absorbing body fluids, a special absorbent article, which has body fluid absorption capacity less than said general absorbent article, and which can be provided for use with the general absorbent article to supplement the body fluid absorption capacity, and a linkage stem body for connecting said general absorbent article to said special absorbent article, wherein said special absorbent article comprises:

a plurality of layers, and at least one of said layers has an elastic recovery sheet for preventing deformation; and a single cover sheet surrounding the plurality of layers and the elastic recovery sheet, and wherein said general absorbent article and said special absorbent article are used respectively solely or in combination, and used appropriately in combination with said linkage stem body.

* * * * *